United States Patent
Falco

(10) Patent No.: US 7,535,411 B2
(45) Date of Patent: May 19, 2009

(54) SYSTEM AND METHOD FOR DETECTING DRIFTS IN CALIBRATED TRACKING SYSTEMS

(75) Inventor: Tony Falco, LaPrairie (CA)

(73) Assignee: Resonant Medical, Inc., Montreal (CA)

( * ) Notice: Subject to any disclaimer, the term of this patent is extended or adjusted under 35 U.S.C. 154(b) by 0 days.

(21) Appl. No.: 11/498,333

(22) Filed: Aug. 1, 2006

(65) Prior Publication Data

US 2007/0034731 A1 Feb. 15, 2007

Related U.S. Application Data

(60) Provisional application No. 60/704,405, filed on Aug. 1, 2005.

(51) Int. Cl.
| G01S 7/40 | (2006.01) |
| A61B 19/00 | (2006.01) |
| G01S 13/06 | (2006.01) |
| G01S 13/88 | (2006.01) |
| G01S 13/00 | (2006.01) |

(52) U.S. Cl. .................. 342/174; 342/61; 342/165; 342/173; 342/175; 342/195; 342/450; 342/451; 702/85; 702/94; 702/95; 702/127; 702/150; 702/152; 600/300; 600/407; 600/424; 606/130

(58) Field of Classification Search .......... 244/3.1–3.3; 702/127, 150–154, 85, 94, 95; 342/27, 28, 342/52–61, 165–175, 195, 73–81, 118, 146–158, 342/450–465; 606/53, 86–88, 130, 1; 700/245–264; 600/407, 410, 414, 424, 425, 426, 300
See application file for complete search history.

(56) References Cited

U.S. PATENT DOCUMENTS

| 5,086,401 | A | * | 2/1992 | Glassman et al. ........... 700/259 |
| 5,299,288 | A | * | 3/1994 | Glassman et al. ........... 700/245 |
| 5,389,101 | A | * | 2/1995 | Heilbrun et al. ............ 606/130 |
| 5,408,409 | A | * | 4/1995 | Glassman et al. ........... 600/407 |
| 5,603,318 | A | * | 2/1997 | Heilbrun et al. ............ 600/426 |
| 5,836,954 | A | * | 11/1998 | Heilbrun et al. ............ 606/130 |
| 6,146,390 | A | * | 11/2000 | Heilbrun et al. ............ 606/130 |
| 6,165,181 | A | * | 12/2000 | Heilbrun et al. ............ 606/130 |
| 6,314,310 | B1 | * | 11/2001 | Ben-Haim et al. .......... 600/424 |
| 6,491,702 | B2 | * | 12/2002 | Heilbrun et al. ............ 606/130 |

(Continued)

FOREIGN PATENT DOCUMENTS

EP    0 951 697 B1    1/1998

(Continued)

OTHER PUBLICATIONS

International Search Report for PCT/CA2006/001289 dated Dec. 1, 2006.

(Continued)

*Primary Examiner*—Bernarr E Gregory
(74) *Attorney, Agent, or Firm*—Goodwin Procter LLP

(57) ABSTRACT

A method and system for detecting drift in calibrated tracking systems used to locate features with respect to one or more coordinate systems allows medical devices to be accurately tracked within a reference coordinate system, and facilitates detection and compensation for changes in the orientation of the tracking system with respect to the coordinate system over time.

28 Claims, 2 Drawing Sheets

U.S. PATENT DOCUMENTS

| | | | |
|---|---|---|---|
| 6,725,079 B2 * | 4/2004 | Zuk et al. | 600/414 |
| 7,092,109 B2 * | 8/2006 | Satoh et al. | 702/153 |
| 2003/0144813 A1 * | 7/2003 | Takemoto et al. | 702/153 |
| 2003/0182072 A1 * | 9/2003 | Satoh et al. | 702/95 |
| 2004/0015075 A1 * | 1/2004 | Kimchy et al. | 600/424 |
| 2004/0176925 A1 | 9/2004 | Satoh et al. | |

FOREIGN PATENT DOCUMENTS

| | | |
|---|---|---|
| EP | 1426806 A2 * | 6/2004 |
| WO | 99/27839 | 6/1999 |

OTHER PUBLICATIONS

Written Opinion for PCT/CA2006/001289 dated Dec. 1, 2006.

* cited by examiner

SYSTEM AND METHOD FOR DETECTING DRIFTS IN CALIBRATED TRACKING SYSTEMS

CROSS-REFERENCE TO RELATED APPLICATIONS

This application claims priority to and the benefit of U.S. provisional patent application Ser. No. 60/704,405, filed Aug. 1, 2005, the disclosure of which is being incorporated herein by reference in its entirety.

FIELD OF THE INVENTION

The present invention relates generally to the field of motion detection, and calibration, and more particularly to a system and method for detecting drift in calibrated tracking systems used to locate features, such as surface elements or markers affixed to or embedded within an object, with respect to one or more coordinate systems.

BACKGROUND OF THE INVENTION

Spatial tracking systems are used for various procedures such as patient surface feature extraction, surgical navigation, or treatment delivery guidance for patient positioning. One critical performance criterion of such systems is their spatial accuracy—i.e., how accurately the tracking systems identify and track the physical location of objects with respect to one or more known reference coordinate systems.

The tracking system is typically composed of an optical tracker anchored to a wall or ceiling of a room, or alternatively placed on a tripod, whose position is calibrated relative to a fixed reference coordinate system. The tracker senses signals (e.g., infrared, magnetic, radio, etc.) that emanate from active markers that are attached to the surface of, or embedded within, the object, or alternatively from passive markers that reflect signals emanating from the tracker itself. Using triangulation techniques, the position and orientation (6 DOF) of the markers, and by proxy the object to which the markers are attached, can be calculated with respect to the optical tracker, and through a transformation, with respect to a fixed reference coordinate system. In other embodiments, the tracker can track surface elements of an object directly without the use of markers, such as in the case of a mounted camera or laser scanning system which images the object's surface elements (e.g. points on a patient's skin) and, through a transformation, calculates the position of these surface elements with respect to a fixed reference coordinate system.

However, the accuracy of such a system depends on maintaining a constant relationship between the fixed coordinate system and the tracking system. If, for example, the tracking system is accidentally knocked out of its calibrated position, or if the tracker drifts over time, inaccuracies may be introduced such that the transformation between the tracker's coordinate system and the fixed coordinate system is no longer accurate. As a result, coordinates assigned to individual features of the object (e.g., marker position, surface, pixels, lesions, etc.) will be misaligned with respect to the fixed coordinate system. Such misalignments can lead to, for example, inaccurate surgical operations or incorrect delivery of radiation treatments, resulting in potentially harmful outcomes.

SUMMARY OF THE INVENTION

The invention provides a method and apparatus to independently monitor a calibrated tracking system in order to detect temporal drifts or accidental collisions that can put the system out of alignment or calibration with respect to a fixed reference coordinate system. The invention may be configured to alert users to such misalignments, to disable related tracked objects such as treatment or imaging devices until such errors are corrected, and in some cases to automatically apply corrective actions by moving the tracking system or adjusting the treatment position or medical image accordingly.

In general, a motion-system device is placed on or about the tracking device prior to, during, or soon after calibration. Once the tracker is calibrated to the fixed coordinate system, the motion-system device continuously or periodically determines if the tracker has moved relative to the fixed coordinate system, and provides feedback to the user and/or a control device. The feedback can be used merely to indicate that a new calibration event is necessary, or in some cases to recalibrate the tracker automatically.

In a first aspect, an apparatus for detecting movement of a tracker with respect to a fixed coordinate system includes a tracker that is calibrated to the coordinate system, and one or more motion-detectors associated with (e.g., mounted on) the tracker. The motion-detector detects movement of the tracker which could potentially affect the calibration of the tracker to the coordinate system.

In some embodiments, the apparatus is located near a hand-held imaging device (e.g., an ultrasound scanner) that includes features on the ultrasound probe, such as markers, that emit or reflect signals (such as infrared signals) that are detected by the tracker. The fixed coordinate system may be defined, for example, by a series of lasers placed about a room, by the physical orientation of a treatment device, by the physical orientation of an imaging device, or by the physical orientation of a patient during a specific medical procedure. The motion-detector may be any suitable device such as a tilt system, an accelerometer, an inclinometer, a magnetometer, wall or ceiling mounted reflective, active markers, or other appropriate devices. In some cases, the apparatus includes a module that alerts a user that the tracker is no longer calibrated to the fixed coordinate system. The alert may be based, in some cases, on the detected movement exceeding a predetermined threshold. In some embodiments, the motion-detector provides a signal to the tracker (or to a control system for positioning the tracker) that may be used to automatically recalibrate the tracker, and/or to compensate for the detected movement.

In another aspect, a method for recalibrating a tracking system to a reference coordinate system includes using a motion-system device to detect alignment errors between the tracker and the fixed coordinate system, and recalibrating (either automatically or manually) the tracker to the fixed coordinate system to reduce or eliminate the alignment errors.

In another aspect, the invention comprises an apparatus for monitoring an object with respect to a first coordinate system. The apparatus can include a tracking system calibrated to the first coordinate system, for tracking the object. The apparatus can also include a motion-detector device associated with the tracking system for detecting a displacement of an element of the tracking system, and a processing device in communication with the motion-detector device and the tracking system. The processing device can be configured to calculate the location of the object with respect to a second coordinate system associated with the tracking system. The processing device can also calculate an adjustment factor based on the detected displacement and adjust the location of the object from the location with respect to the second coordinate system into a location with respect to the first coordinate system in accordance with the adjustment factor.

In one embodiment, the adjustment factor is a transformation. The tracking system can be configured to detect features associated with the object. The features can be embedded within the object. Alternatively, the features can be located on the surface of the object. The object may include a surface characteristic of a patient, such as, for example, the facial features, shape of the torso or other part of the body, or dye marks on the skin.

In one embodiment, the features may include at least one active marker, such as, for example, an emitter, an optical source, an acoustic source, a magnetic source, an electronic marker, an acoustical marker, a magnetic marker, a radiofrequency marker, a radioactive marker, and a radioactive source. The features can also include at least one passive marker, such as, for example, a reflector or a radio-opaque fiducial marker embedded in the object (e.g. patient) or placed on the surface of the object. The object can include, for example, one of a medical device, a patient's surface, a surgical navigation tool, a diagnostic device, a portable device, and a treatment device. In one embodiment, the object comprises an anatomical feature of a patient. The anatomical feature may be an external feature of the patient, or an internal feature of the patient. The tracking system can include, for example, one or more of an optical camera, a magnetic tracker, an infrared camera, a radiofrequency based tracker, and a laser-based surface scanning device. The medical device, diagnostic device or treatment device can be selected, for example, from the group consisting of, but not limited to, a thermal device, a radiation device, a surgical device, a mechanical device, and an ultrasound device.

In one embodiment of the invention, the first coordinate system can be defined by a plurality of lasers placed about a room. The first coordinate system can be defined by one of a physical orientation of a medical device, a diagnostic device, a treatment device or a patient position. The motion-detector device can include one of a tilt system, an accelerometer, an inclinometer, a magnetometer, or a set of mountable markers. The mountable markers may be mounted to walls of a room, and/or mounted to components of a room such as the treatment table.

One embodiment can include an alert module for alerting a user of the apparatus of a movement of the tracking system. The alert may be based on the detected movement exceeding a predetermined threshold. The apparatus can also include a position-adjustment device. The processing device can provide a signal to the position-adjustment device such that the positioning device adjusts the position of the tracking system, thereby bringing the tracker into calibration with the first coordinate system. The apparatus can also include a control device for controlling the operation of one or more object of a medical device, treatment device and diagnostic device.

In another aspect, the invention comprises a method of recalibrating a position-tracking device to a reference coordinate system. The method can include the steps of calibrating a position and orientation of a position-tracking device to a reference coordinate system, using a motion-sensor device to detect alignment errors between the position-tracking device and the fixed coordinate system, and recalibrating the position and orientation of the position-tracking device to the reference coordinate system to reduce the alignment errors.

In one embodiment, the alignment error can consist of at least one directional component of translation and/or rotation. The method can include the step of adjusting the position and orientation of the tracking system to correct alignment errors. The adjusting step can be carried out automatically in response to the detection of an alignment error, or be carried out manually by a user. The method can also include the step of disabling the object (e.g. medical device) being tracked by the tracking system upon the detection of an alignment error.

In still another aspect, the invention comprises a means for monitoring an object with respect to a first coordinate system. The means comprises; calibrating a position and orientation of a position-tracking device to a reference coordinate system, detecting motion-based alignment errors between the position-tracking device and the fixed coordinate system, and, based on the detected alignment errors, recalibrating the position and orientation of the position-tracking device to the reference coordinate system to reduce the alignment errors.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Figure 1:
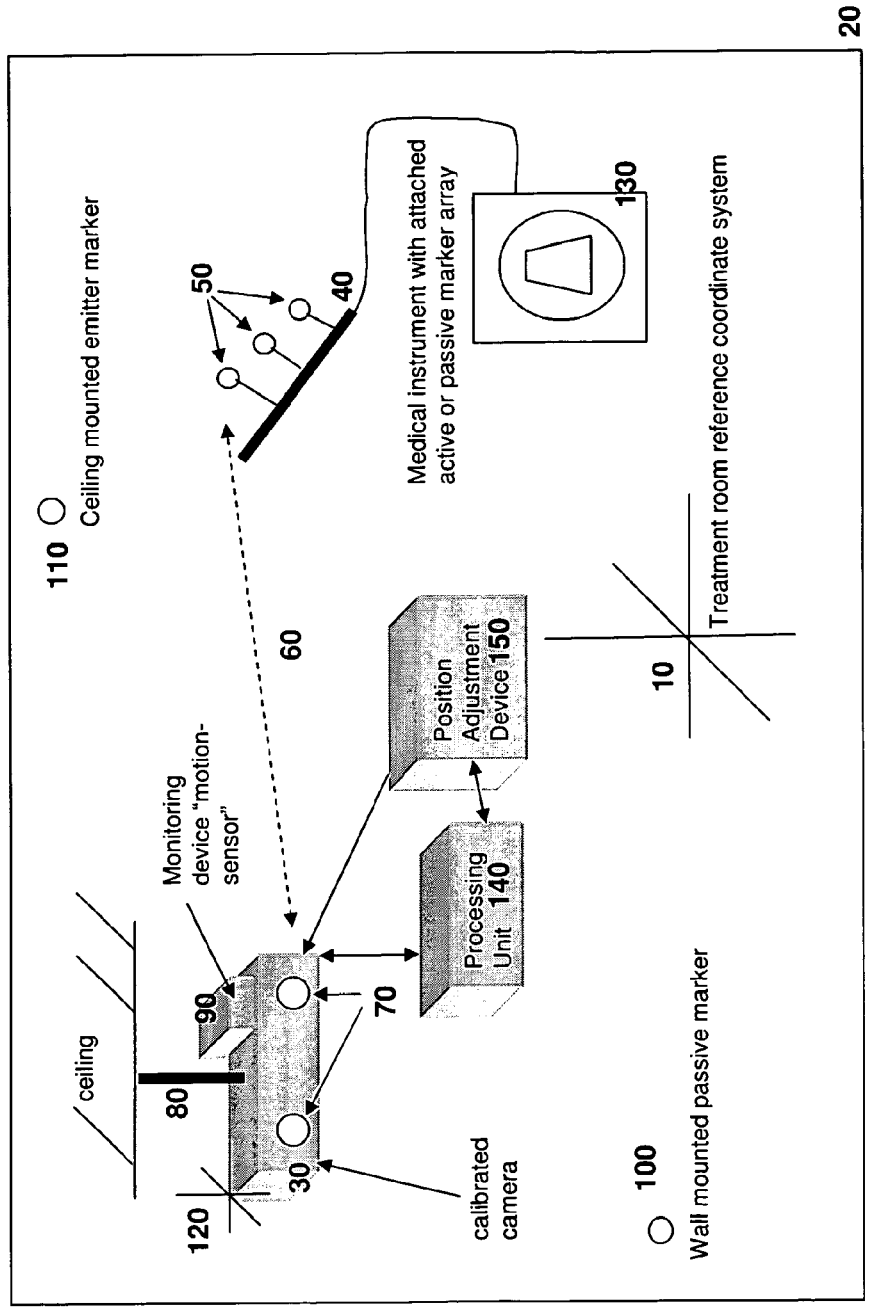
FIG. 1 is a schematic view of an example calibrated tracking system in accordance with one embodiment of the invention.

The invention provides a method and apparatus for monitoring a calibrated position-tracking system for use in tracking the location of features of an object with respect to a reference coordinate system.

The tracking system may be used to track the location of any feature of an object such as the surface of an object or features such as passive or active markers associated with a medical device, for use in the diagnosis and/or treatment of a patient, where it is advantageous or necessary to accurately locate, and/or record the location of, the medical device.

To accurately track the location of an object such as a medical device, features such as a marker, or an array of markers, are located within or upon the tracked object to transmit a constant signal, or a discrete repeated signal at regular intervals. The tracked features such as markers may transmit or reflect a signal such as an infrared, magnetic, radio, light, or other electromagnetic signal, that allow as tracking system to sense and record the location of the tracked object within a given coordinate system. The markers may be configured to send out a single signal, or to send out multiple signals at different frequencies. By sensing the one or more signals transmitted from the one or more features located on or within the tracked object, the tracking system may calculate (using standard methods such as triangulation) and record the location of the object as its position moves with respect to the tracking system and by extension moves with respect to a reference coordinate system to which the tracking system is calibrated to.

In one embodiment, an omni-directional signal is transmitted from the markers and/or location emitter(s) within the object, allowing the transmitted signal to be received by a tracking system regardless of the position and orientation of the object. Alternatively, the markers and/or emitter(s) may be configured to transmit a directionally discrete signal towards the tracking system.

In one embodiment of the invention, a tracking system may be used to sense and record the location of the tracked object.

This tracking system may include one or more receivers positioned at discrete locations within, and/or about, a given coordinate system. The receiver, or receivers, may include infrared, acoustic, radio, visible light, and/or other appropriate signal measuring devices capable of sensing a signal emitted or reflected by one or more markers. In one embodiment, the receiver is configured to only receive signals at a single set frequency. In an alternative embodiment, the receiver is configured to receive a variety of signals. The tracking system may include a single receiving unit, or include a number of separate individual receiving units, connected to a processing unit.

By sensing the one or more signals emitted or reflected from the one or more markers associated with the object, the tracking system may calculate (using standard triangulation methods) and record the location of the object as its position moves with respect to the signal-receiving unit of the tracking system. This position data may be communicated to the operator of the object, thus allowing the operator to accurately locate the portable device at any position with respect to the receiver of the tracking system. The position data may be communicated through a visual display, audio signal, or combination of the two. In one embodiment of the invention, the markers are permanently attached to the tracked object. In an alternative embodiment, an emitter array is releasably attached to any portable device, allowing multiple devices to be used within a treatment room using a single marker array.

In one embodiment of the invention, the tracking system may be located at a set location within or surrounding a separately defined coordinate system. For example, the tracking system may include one or more receiving units placed on or mounted to the walls of a room, with a coordinate system defined by the walls. As such, if the location and orientation of the receiving unit (or units) of the tracking system are known, the tracking system can convert the position data of the object from a location based on the coordinate system defined by the tracking system to a location based on the room coordinates. This can allow the object to be accurately positioned and oriented with respect to any known location within the room.

The tracking system and/or the room may be defined by a Cartesian coordinate system, a cylindrical coordinate system, and/or a spherical coordinate system. For example, in one embodiment of the invention, the tracking system calculates the location of the portable device with respect to a receiving unit in spherical coordinates, and then converts this position into a location within a room defined by cartesian coordinates. The (x, y, z) axes of the room-based cartesian coordinate system may correspond, for example, with the floor and walls of the room, with the center of the coordinate system (i.e., the (0, 0, 0) location) being positioned either at a corner of the room, or at some other defined point within the room. In one embodiment, the center of a room-based cartesian coordinate system may be located at a set point on a treatment table fixedly positioned within the room. Thus, the tracking system can allow a user to position a portable device accurately with respect to the treatment table, allowing for improved medical diagnosis and treatment using portable devices.

Objects such as medical devices that may be advantageously used with this tracking system include, but are not limited to, ultrasound devices, laser measurement (such as surface scanning laser devices), camera devices, and/or treatment devices, portable devices, trackers, cutting implements or other invasive medical devices, x-ray equipment, optical probes, thermal measurement and/or treatment devices, magnetic devices, or any other appropriate device or implement for use in medical diagnosis and/or treatment (such as an x-ray system for locating markers or fiducials embedded within a patient). The tracking system may be configured to track a single medical device in a given coordinate system, track multiple devices simultaneously, and/or switch between the tracking of different medical devices. The tracking system can also be used to confirm the location of other devices within a room, such as, but not limited to, robotic arms or other movable equipment mounted, either fixedly or releasably, to a fixture of the treatment room.

In one embodiment of the invention, calibrated tracking systems may be placed at one or more locations on one or more of the walls, ceiling, and floor of a room to measure the dimensions of the room and monitor the geometry of the room over time. As such, changes in the size and/or shape of a room over time, due to settling or other structural changes in the building, or due to the effects of earthquakes or other natural phenomena, may be monitored with the motion-detector and compensated for when determining the new dimensions of the room. In one embodiment, the tracking system tracks features on the walls of the room (e.g. fixed passive or active markers attached to the walls) that can transmit a signal to the tracking system. As such, the tracking system can monitor the location of these stationary emitters to monitor any relative movement of the walls of the room and tracker over time. Alternatively, the relative positions of the wall markers may be monitored by a signal being emitted from the tracking system, with a reflected signal, or separate return signal, being initiated by the wall emitters or markers.

In one exemplary embodiment, active and/or passive systems are placed on the walls, floor, and/or ceiling of a medical treatment room, and are generally fixed in position about the room with respect to a calibrated tracking system. The tracking system, includes an optical tracker that, during imaging, tracks additional devices attached to a medical instrument (e.g., an ultrasound probe for generating reconstructed 3D images, or a surgical device) to track the location of the instrument with respect to the optical tracker during use. From time to time, the tracker may verify that its position in space has not changed relative to the position of the markers affixed to the room walls or ceiling. One example of such a calibrated positioning system includes optical trackers such as the POLARIS system from Northern Digital Inc. of Waterloo, Ontario, Canada.

However, monitoring the dimensions of the room over time may be important to ensure that the tracking device remains calibrated with respect to the coordinate system for the room. For example, structural changes in the building over time, earthquakes or other natural phenomena, experimental drift of the tracking system, user interference (such as, but not limited to, movement of the tracking system during cleaning and/or maintenance), or any other phenomena affecting the orientation and/or location of the tracking system, can change the spatial relationship between the coordinate system associated with the tracking system and the coordinate system associated with the room. As a result, an error can result when converting the position of the portable device, or other object, from the tracking system coordinates to the room coordinates, which can therefore result in an incorrectly positioned device. This can obviously be dangerous when using a portable device in medical diagnosis and/or treatment. Thus, it is important to ensure that the relationship between the tracking system coordinates and the room coordinates is known and/or maintained after initial calibration (as well as between periodic calibrations) of the tracking system.

In order to maintain an accurate calibration of the tracking system over time and in accordance with various embodiments of the invention, the location and orientation of the tracking system may be monitored and, if necessary, adjusted and/or compensated for. This may be achieved, in one embodiment, by attaching a motion-sensitive device to the tracking system to locally monitor the position, status, and/or orientation of the tracking system. The invention therefore provides apparatus and methods for detecting such changes by associating an independent motion detector with the tracker to detect changes in its location over time. Examples of suitable motion detectors include the CTX family of tilt systems manufactured by Crossbow Technology Inc. of San Jose, Calif. In other embodiments, the motion-detection device uses a series of active and/or passive systems tracked by the tracker and placed on walls, ceiling and/or floor of a treatment room with respect to the fixed calibration system.

In one embodiment, servo-motors, or other appropriate position adjustment devices 150, may be incorporated into the tracking system to actively return the tracking system to its original position and/or orientation if a movement is detected by a motion detector. As a result, the relationship between the tracking system coordinates and the room coordinates may be maintained. This may be achieved automatically by the tracking system controls, or be carried out in response to a user input.

In an alternative embodiment, a change in position and/or orientation of the tracking system is compensated for by applying correction factors to the equations used to convert the new location of a medical device from tracking-system coordinates to room coordinates. In this embodiment, a motion system can send a signal to the tracking system controls indicating when a movement of the tracking-system has occurred, and providing information such as the magnitude and/or direction of such movement. The tracking-system control may then calculate an appropriate correction factor, which is applied to the coordinate conversion calculations, thus ensuring the accuracy of the location of a medical device with respect to the room coordinates.

FIG. 1 illustrates one non-limiting example of a tracking system in accordance with one embodiment of the invention. A reference coordinate system 10 is defined (e.g. by orthogonal room lasers in a radiotherapy treatment room or by a surgical navigational emitter array in an operating room) in a treatment room 20. A tracking system 30 is located within the room 20 to track, record, and display the position of an object 40 (e.g., surgical instrument or "free-hand" tracked ultrasound probe for 3D imaging) that may be used in the treatment of a patient in the treatment room 20. The tracked object 40 may include any one or more of the functions described above. The tracked object 40 includes a number of features such as passive or active markers 50 that can transmit or reflect a signal 60 to the tracking sensor 70 of the tracking system 30, in order to indicate the location (either continuously or periodically) of the tracked object 40 related to the reference coordinate system 10. The tracking system 30 is mounted by a bracket 80 to the ceiling of the room 20. A motion-detector 90 monitors at least one, but preferably all, translational or rotational components of the location and orientation of the tracking system(s) 30.

The room 20 is defined by a reference coordinate system 10. One or more wall-mounted markers (or emitters) are positioned on the wall 100 and ceiling 110 of the room 20 as an alternative tracking system motion-detection method, whereby, movement of the calibrated tracking system relative to the wall-mounted markers would indicate misalignment of the tracking system. In operation, the tracking system 30 is calibrated to correctly convert the location of the object 40 from the tracking-system's coordinate system 120 to the room's coordinate system 10. Once this calibration has been completed, the tracking system 30 can receive the signals 60 emitted from the array of markers 50 on the object 40, and send this information to a processing unit 140. The processing unit 140 then calculates the position of the object 40 in the room coordinates 10.

Over time, as described above, a misalignment of the tracking sensor 70 may occur, due to disturbance of the tracking system 30 during cleaning or maintenance, movement of the building caused by settling of the foundations of the building over time or as a result of natural phenomena such as earthquakes, vibrations caused by the buildings HVAC system or from a nearby train track or roadway, or experimental drift of the system. Compensation for such changes can be determined by monitoring the orientation and position of the tracking system 30 or sensor 70 through a motion detector 90 placed on or within the tracking sensor 70 (or through wall-mounted markers). If any change in position and/or orientation is detected by the motion detector 90, the tracking system 30 can be made to compensate for this by, for example, adjusting values of conversion factors used to calculate the location of the medical device 40 in the room-based coordinates 10. Alternatively, the tracking system 30 can be connected to a number of servo-motors, or other electrical or mechanical adjustment means (not shown), to realign the tracking sensor 70 if any disturbance in its position or orientation is detected. A signal may also be sent to a user of the portable device 40, either through a warning message being displayed on a display unit or by an audible warning signal being broadcast, if a misalignment has been detected. In some cases, the motion detector 90 can only detect a limited number of degrees of freedom of position and rotation. For example, an accelerometer can measure two out of three degrees of rotation, and can not measure translational motion. Such partial motion information is useful to alert the user to of most probable misalignments, but is not sufficient on its own to correct for misalignments in all 6 DOF. In some cases, multiple motion detectors 90, each with different degrees of freedom detection capabilities, can be combined to capture all possible types of tracking system 30 misalignment and fully correct for such misalignment.

In addition, the tracking system 30 can monitor the locations of the wall 100 or ceiling 110-mounted emitters/markers with respect to the tracking sensor 70, for example, by receiving (via the tracking sensor 70, for example) a location signal broadcast from each wall-100 or ceiling 110-mounted emitter or transmitter markers. As a result, the tracking system 30 can monitor the positional relationship between the tracking sensor 70 and the room 20 and compensate for any slight movement of the tracking sensor 70 and/or one or more walls of the room 20 over time. In one embodiment, additional systems (similar to, or different from, wall-mounted systems 120 as desired) may be placed on other components of the room (such as the treatment table), thereby allowing the tracking system to monitor the positional relationship between the tracking sensor 70 and the treatment room component (not shown) over time. It is to be understood that the present invention may be applied to detecting calibration errors, by periodically monitoring 90 the position of the tracker 30 for virtually any tracking device (e.g., optical, magnetic, mechanical, laser surface tracker, etc) in essentially any environment.

In one example embodiment, the invention may involve a tracking sensor including a wall or ceiling-mounted optical camera used to calibrate images taken using a hand-held ultrasound imaging probe to a three-dimensional reference coordinate system defined in a radiation treatment room. However, it is to be understood that the present invention may be applied to detecting calibration errors for virtually any tracking device (e.g., optical, magnetic, mechanical, etc) in essentially any environment. A camera tracking/positioning system may be calibrated to a treatment room coordinate system (e.g., an operating room or radiotherapy treatment room) and tracks a medical device (e.g., surgical instrument or ultrasound probe for 3D imaging) relative to the treatment room coordinate system. An independent monitoring device, e.g. a tilt detector, may be attached to the calibrated camera and periodically monitor the position of the camera.

Figure 2:
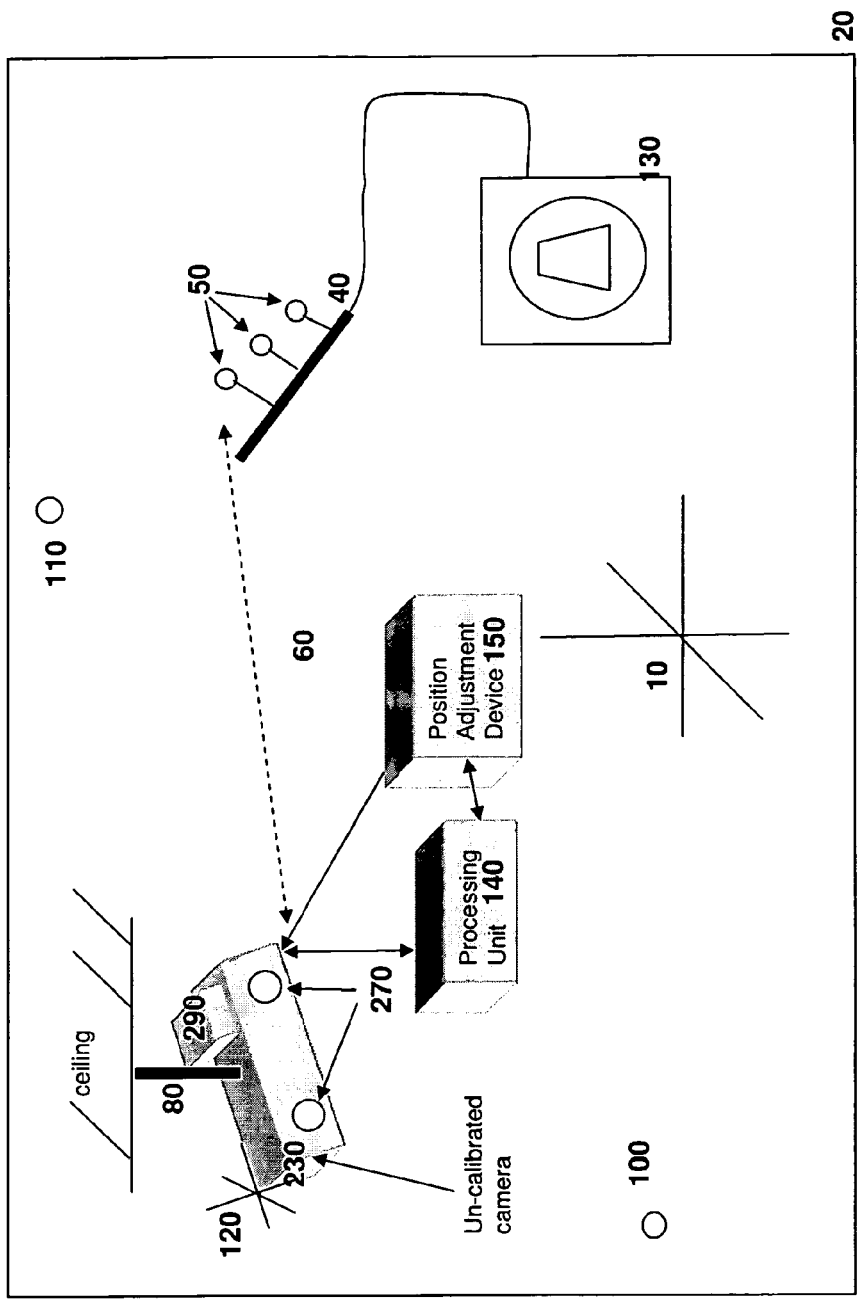
FIG. 2 is a schematic view of the apparatus including the tracking system and the motion-sensor device of FIG. 1 with the tracking system misaligned from its originally calibrated position.

Referring to FIG. 2, one or more events such as physical collision with another object or person, slight drifts of the tracker 230 housing or internal components 270, and/or shifts in the building itself may cause the tracker 230 to become misaligned with respect to the room coordinate system 10 to which it was originally calibrated. Because the tracker 230 has moved from its calibrated position 30, it can no longer effectively determine the position of the medical instrument 40 relative to the room coordinate system 10, and therefore any treatments administered to the patient that rely on the positioning of such instruments are compromised.

By determining that the tracker 230 is out of alignment (and therefore un-calibrated), the tilt detector 290 may, for example, alert the operator that a misalignment exists and recalibration is necessary. Further, the tilt detector 290 may also send instructions (via, for example, wireless or wired communications) to one or more components of the imaging or surgical apparatus 40 (e.g., to halt operations), thus preventing further treatment until the tracker 230 is re-calibrated to the room coordinate system 10.

In another embodiment, the optical tracker 30 (or 230) is mounted on a mechanical positioning device that accepts instructions from the tilt detector 90 (or 290). In such instances, the instructions may include corrective information relating to the misalignment, thus providing the necessary commands to move the mechanical positioning device back to its original, calibrated position. In other embodiments, the corrective information may be forwarded to the imaging system or medical device 130 and used to compensate for the misalignment when locating devices or registering images to the reference coordinate system 10. Additional monitoring of the optical trackers 30 (or 230) and in particular their positions and orientations 120 with respect to the room coordinate system 10, may be carried out by monitoring the location of the tracker 30 (or 230) with respect to a number of wall-mounted 100 or ceiling-mounted 110 emitters positioned a set locations around the room, as described above.

The invention may be embodied in other specific forms without departing form the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. An apparatus for monitoring a medical object with respect to a first coordinate system, the apparatus comprising:
   a tracking system calibrated to the first coordinate system, for tracking the medical object;
   a motion-detector device associated with the tracking system for detecting a displacement of an element of the tracking system; and
   a processing device in communication with the motion-detector device and the tracking system, the processing device configured to:
   calculate the location of the medical object with respect to a second coordinate system associated with the tracking system;
   calculate an adjustment factor based on the detected displacement;
   disable the medical object; and
   adjust the location of the medical object from the location with respect to the second coordinate system into a location with respect to the first coordinate system in accordance with the adjustment factor.

2. The apparatus of claim 1, wherein the adjustment factor is a transformation.

3. The apparatus of claim 1, wherein the tracking system is configured to detect features associated with the medical object.

4. The apparatus of claim 3, wherein the features are embedded within the medical object.

5. The apparatus of claim 3, wherein the features are located on the surface of the medical object.

6. The apparatus of claim 3, wherein the features comprise at least one active marker.

7. The apparatus of claim 6, wherein the at least one active marker comprises at least one of an optical marker, an acoustic marker, a magnetic marker, a radioactive electronic marker, or a radiofrequency emitter.

8. The apparatus of claim 3, wherein the features comprise at least one passive marker.

9. The apparatus of claim 8, wherein the at least one passive marker comprises at least one of a reflector, an electronic marker, an acoustical marker, a magnetic marker, or a radioactive marker.

10. The apparatus of claim 1, wherein the medical object comprises at least one of a medical device, a surgical navigation tool, a diagnostic device, or a treatment device.

11. The application of claim 1, wherein the medical object comprises an anatomical feature of a patient.

12. The apparatus of claim 11, wherein the anatomical feature comprises an external feature of the patient.

13. The apparatus of claim 11, wherein the anatomical feature comprises an internal feature of the patient.

14. The apparatus of claim 1, wherein the tracking system comprises at least one of an optical camera, a magnetic tracker, an infrared camera, a radiofrequency based tracker, or a laser-based surface scanning device.

15. The apparatus of claim 1, wherein the first coordinate system is defined by a plurality of lasers placed about a room.

16. The apparatus of claim 1, wherein the first coordinate system is defined by one of a physical orientation of a medical device, a diagnostic device, a treatment device or a patient position.

17. The apparatus of claim 1, wherein the motion-detector device comprises at least one of a tilt system, an accelerometer, an inclinometer, a magnetometer, or a set of mountable markers.

18. The apparatus of claim 1, wherein the motion-detector device further comprises an alert module for alerting a user of the apparatus of a movement of the tracking system.

19. The apparatus of claim 18, wherein the alert is based on the detected movement exceeding a predetermined threshold.

20. The apparatus of claim 1, further comprising a position-adjustment device.

21. The apparatus of claim 20, wherein the processing device provides a signal to the position-adjustment device, the positioning device adjusting the position of the tracking system in response to the signal, thereby bringing the tracker into calibration with the first coordinate system.

22. The apparatus of claim 1 wherein the processing device is further configured to enable the medical object once recalibrated.

23. A method of recalibrating a position-tracking device to a reference coordinate system, the method comprising the steps of:
   calibrating a position and orientation of a position-tracking device to a reference coordinate system;
   detecting motion-based alignment errors between the position-tracking device and the fixed coordinate system;
   disabling a medical object being tracked by the position-tracking device upon detection of the alignment errors; and
   based on the detected alignment errors, recalibrating the position and orientation of the position-tracking device to the reference coordinate system to reduce the alignment errors.

24. The method of claim 23 wherein the alignment errors consist of at least one directional component of translation or rotation.

25. The method of claim 23, further comprising the step of adjusting the position and orientation of the tracking system to correct the alignment errors.

26. The method of claim 23, wherein the adjusting step is carried out automatically in response to the detection of an alignment error.

27. The method of claim 23, wherein the adjustment step is carried out manually by a user.

28. The method of claim 23 further comprising enabling the medical object after the recalibration step.

* * * * *